United States Patent [19]

Hooper et al.

[11] 4,322,308

[45] * Mar. 30, 1982

[54] DETERGENT PRODUCT CONTAINING DEODORANT COMPOSITIONS

[75] Inventors: David C. Hooper, Ashford; George A. Johnson; Donald Peter, both of Wirral, all of England

[73] Assignee: Lever Brothers Company, New York, N.Y.

[ * ] Notice: The portion of the term of this patent subsequent to Sep. 8, 1998, has been disclaimed.

[21] Appl. No.: 117,724

[22] Filed: Feb. 1, 1980

Related U.S. Application Data

[63] Continuation-in-part of Ser. No. 77,709, Sep. 21, 1979, abandoned, which is a continuation-in-part of Ser. No. 878,092, Feb. 15, 1978, abandoned, which is a continuation-in-part of Ser. No. 933,931, Aug. 15, 1978, Pat. No. 4,289,641.

[30] Foreign Application Priority Data

Feb. 15, 1977 [GB] United Kingdom ................. 6249/77
Jan. 12, 1978 [GB] United Kingdom ................. 1285/78

[51] Int. Cl.$^3$ ........................... C11D 9/44; C11D 9/50
[52] U.S. Cl. .................................. 252/107; 252/106; 252/132; 252/174.11
[58] Field of Search ............ 252/106, 107, 132, 174.11

[56] References Cited

U.S. PATENT DOCUMENTS

| | | | |
|---|---|---|---|
| 2,875,131 | 2/1959 | Carpenter et al. | 252/522 X |
| 2,889,254 | 6/1959 | Fiore et al. | 252/522 X |
| 2,918,412 | 12/1959 | Wood | 252/522 X |
| 2,976,321 | 3/1961 | Dorsky et al. | 252/522 X |
| 3,317,397 | 5/1967 | Saunders | 252/108 X |
| 3,318,945 | 5/1967 | Erman | 260/468 |
| 3,591,643 | 7/1971 | Fanta et al. | 260/617 F |
| 3,662,007 | 5/1972 | Fanta et al. | 260/631.5 |
| 3,679,756 | 7/1972 | Kretschmar et al. | 260/631.5 |
| 3,969,259 | 7/1976 | Lages | 252/107 |
| 3,975,309 | 8/1976 | Kulka et al. | 252/522 |

FOREIGN PATENT DOCUMENTS

| | | |
|---|---|---|
| 7604601 | 8/1977 | Brazil . |
| 2440025 | 3/1975 | Fed. Rep. of Germany . |
| 2454969 | 5/1975 | Fed. Rep. of Germany . |
| 2455761 | 6/1976 | Fed. Rep. of Germany . |
| 858826 | 1/1961 | United Kingdom . |
| 1085940 | 10/1967 | United Kingdom . |
| 1197817 | 7/1970 | United Kingdom . |
| 1266060 | 3/1972 | United Kingdom . |
| 1282889 | 7/1972 | United Kingdom . |
| 1302933 | 1/1973 | United Kingdom . |
| 1359492 | 7/1974 | United Kingdom . |
| 1420949 | 1/1976 | United Kingdom . |

OTHER PUBLICATIONS

"Handbuch der Kosmetika and Reichstoffe, Band 2", H. Janistyn, 1969.
"Handbuch der Gesamten parfumerie and Kosmetik", Fred Winter, 1952, pp. 735–754.
Sagarin, "Cosmetics–Science & Technology" (M. S. Balsana), Chapter 32, 1972, pp. 599 and 608–621.

*Primary Examiner*—P. E. Willis, Jr.
*Attorney, Agent, or Firm*—James J. Farrell; Melvin H. Kurtz

[57] ABSTRACT

A deodorant detergent composition comprises a detergent-active compound and a deodorizing amount of a deodorant perfume and a deodorant other than a deodorant perfume, the composition having an odor reduction value within the range of from 0.50 to 3.5 as measured by the Odor Reduction Value Test.

19 Claims, No Drawings

DETERGENT PRODUCT CONTAINING DEODORANT COMPOSITIONS

This application is a continuation-in-part application jointly of applicants' co-pending application Ser. No. 77,709 filed Sept. 21, 1979 now abandoned which is a continuation-in-part application of application Ser. No. 878,092 filed Feb. 15, 1978 now abandoned, and of applicants' co-pending application Ser. No. 933,931 filed Aug. 15, 1978, now Pat No. 4,289,641.

This invention relates to deodorant compositions for use in suppressing human body malodour.

BACKGROUND OF THE INVENTION

It has long been recognized that the development of body malodours is at least partly due to bacterial action on the products of the sweat glands. Washing with a detergent, for instance in the form of a personal washing bar such as a soap bar, removes malodorous products and reduces the concentration of bacteria on the skin. Complete elimination of bacteria cannot usually be achieved by this means and for this reason it has also been customary to incorporate germicides into detergent compositions for personal washing in the belief that growth of those skin microflora that contribute to body malodour can be inhibited and the production of malodorous substances suppressed by them. Such germicides are at least partly effective in reducing or retarding the development of body malodour, but they do not completely solve the problem, possibly because there are other causes of malodour development on the skin which are unrelated to the proliferation of bacteria.

The limited effectiveness of germicides as the sole deodorant agent in a soap bar in combating the problem of body malodour can be demonstrated by determining the reduction in the intensity of body malodour obtained when standard soap bars containing different levels of germicide are compared by a test based on that devised by Whitehouse and Carter as published in The Proceedings of the Scientific Section of the Toilet Goods Association, Number 48, December 1967 at pages 31–37 under the title "Evaluation of Deodorant Toilet Bars". Details as to how this test is conducted are given later in this specification under the heading "Odour Reduction Value Test" but it can be stated now that when this modified test is employed using, for example the germicide 3,4,4'-trichlorocarbanilide instead of deodorant perfume, it has been possible to demonstrate that the maximum reduction in odour intensity obtainable (i.e. the numerical difference between the scores attributed to the test soap bar with germicide and the control soap bar without germicide, hereinafter referred to as the odour reduction value) is not greater than about 0.4, irrespective of the amount of the germicide in the test soap bar.

Typical results are summarised in the following Table.

TABLE 1

The effect of 3,3,4'-trichloro-carbanilide on the reduction of odour intensity when tested against control soap bars containing no germicide

| Wt % germicide in soap bar | Odour Reduction Value |
| --- | --- |
| 0.16 | 0.10 |
| 0.25 | 0.14 |
| 0.5 | 0.22 |
| 0.75 | 0.27 |
| 1.0 | 0.30 |

TABLE 1-continued

The effect of 3,3,4'-trichloro-carbanilide on the reduction of odour intensity when tested against control soap bars containing no germicide

| Wt % germicide in soap bar | Odour Reduction Value |
| --- | --- |
| 2.0 | 0.37 |

Similar results are obtained if a mixture of two or more germicides, for example 3,4,4'-trichloro-carbanilide and 3,5,4'-tribromo-salicylanilide, are tested in the same way: the maximum odour reduction value obtainable is still only about 0.4.

Perfumes have been used as odour maskants since ancient times, and it is customary to incorporate perfumes into detergent compositions for personal washing such as soap bars, though these perfumes are in general ineffective in preventing the development of malodour.

In Brazilian Patent Application No. PI 7604601 published Aug. 16, 1977, perfumes having deodorant properties are described. These perfumes can be incorporated into detergent compositions such as soap which when applied to human skin can reduce body malodour. The materials contained within these perfumes which are collectively responsible for their deodorant property can be identified as satisfying either or both of two tests known respectively as the Lipoxidase Test and the Morpholine Test. The conduct of these Tests is fully described in the specification of the Brazilian patent application and is reproduced in full herewith for the sake of completeness.

It has now been discovered that certain combinations of perfume materials, hereinafter referred to as deodorant perfumes, when incorporated into detergent compositions containing a conventional germicide for personal washing provide a more effective means for inhibiting malodour development than the use of such a germicide alone, in that the odour reduction value, as measured according to the Odour Reduction Value Test, can exceed 0.4. This effect is clearly not solely one of odour masking, since in many instances there is no detectable smell of the perfume on the treated skin after a few hours. Accordingly, the use of deodorant perfumes and germicides in deodorant compositions represents a new operative principle.

In the course of attempts to characterise this new principle, many hundreds of known perfume materials have been screened. Hundreds of formulations made by blending materials have been examined, including a number of commercial perfumes whose formulations are not fully known (being confidential to the perfumery house in question offering the perfume for sale). No commercial perfume has been found that is capable of giving a germicide-containing soap bar the malodour-inhibiting property attributable to a mixture of germicide and deodorant perfume. This supports the view that a new principle of an entirely unexpected kind has been discovered.

DEFINITION OF THE INVENTION

In its widest aspect, the invention provides a deodorant detergent composition comprising detergent active compound, a deodorant perfume, and a deodorant other than deodorant perfume, the composition having an odour reduction value in the range of from 0.50 to 3.5 as measured by the Odour Reduction Test.

The invention also provides a process for preparing a deodorant detergent composition which process comprises mixing a deodorant perfume and a deodorant other than a deodorant perfume and a detergent-active compound to provide a deodorant detergent composition having an odour reduction value within the range of from 0.50 to 3.5 as measured by the Odour Reduction Test.

The invention furthermore provides a method for suppressing body malodour, particularly of human origin, which comprises applying to the skin or hair an effective amount of a deodorant detergent composition, said composition comprising detergent active compound, a deodorant perfume, and a deodorant other than deodorant perfume, the composition having an odour reduction value within the range of from 0.50 to 3.5 as measured by the Odour Reduction Test.

Detergent Active Compound

The composition will contain a soap or a non-soap detergent active, or both a soap and a non-soap detergent active.

The soap is a water-soluble or water-dispersible alkali metal salt of an organic acid, especially a sodium or a potassium salt, or the corresponding ammonium or substituted ammonium salt. Examples of suitable organic acids are natural or synthetic aliphatic carboxylic acids of from 10 to 22 carbon atoms, especially the fatty acids of triglyceride oils such as tallow and coconut oil.

The preferred soap is a soap of tallow fatty acids, that is fatty acids derived from tallow class fats, for example beef tallow, mutton tallow, lard, palm oil and some vegetable butters. Minor amounts of up to about 30%, preferably 10 to 20%, by weight of sodium soaps of nut oil fatty acids derived from nut oils, for example coconut oil and palm kernel oil, may be admixed with the sodium tallow soaps, to improve their lathering and solubility characteristics if desired. Whereas tallow fatty acids are predominantly $C_{14}$ and $C_{18}$ fatty acids, the nut oil fatty acids are of shorter chain length and are predominantly $C_{10}$–$C_{14}$ fatty acids.

The non-soap detergent active can be a non-soap anionic or a nonionic or a cationic or an amphoteric or a Zwitterionic compound. Typical non-soap anionic detergent-active compounds include water-soluble salts, particularly the alkali metal, ammonium and alkanolammonium salts, of organic sulphuric reaction products having in their molecular structure an alkyl group containing from about 8 to about 22 carbon atoms and a sulphonic acid or sulphuric acid ester group. (Included in the term "alkyl" is the alkyl portion of actyl groups). Examples of this group of non-soap detergent active which can be used are the sodium and potassium alkyl sulphates, especially those obtained by sulphating the higher alcohols ($C_8$–$C_{18}$ carbon atoms) produced by reducing the glycerides of tallow or coconut oil; and sodium and potassium alkyl benzene sulphonates, in which the alkyl group contains from about 9 to about 15 carbon atoms in straight chain or branched chain configuration.

Other anionic detergent-active compounds include the sodium alkyl glycerol ether sulphonates, especially those ethers of higher alcohols derived from tallow and coconut oil; sodium coconut oil fatty acid monoglyceride sulphonates and sulphates; and sodium or potassium salts of alkyl phenol ethylene oxide ether sulphate containing about 1 to about 10 units of ethylene oxide per molecule and wherein the alkyl groups contain about 8 to about 12 carbon atoms.

Other useful non-soap anionic detergent-active compounds include the water-soluble salts of esters of α-sulphonated fatty acids containing from about 6 to about 20 carbon atoms in the ester group; water-soluble salts of 2-acyloxy-alkane-1-sulphonic acids containing from about 2 to 9 carbon atoms in the acyl group and from about 9 to about 23 carbon atoms in the alkane moiety; alkyl ether sulphates containing from about 10 to 20 carbon atoms in the alkyl group and from about 1 to 30 moles of ethylene oxide; water-soluble salts of olefin sulphonates containing from about 12 to 24 carbon atoms; and 6-alkyloxy alkane sulphonates containing from about 1 to 3 carbon atoms in the alkyl group and from about 8 to 20 carbon atoms in the alkane moiety.

Preferred water-soluble non-soap anionic detergent-active compounds include linear alkyl benzene sulphonates containing from about 11 to 14 carbon atoms in the alkyl group; the tallow range ($C_{12-20}$) alkyl sulphates; the coconut range alkyl glyceryl sulphonates; and alkyl ether sulphates wherein the alkyl moiety contains from about 14 to 18 carbon atoms and wherein the average degree of ethoxylation varies between 1 and 6.

Specific preferred non-soap anionic detergent-active compounds include: sodium linear $C_{10}$–$C_{12}$ alkyl benzene sulphonate; triethanolamine $C_{10}$–$C_{12}$ alkyl benzene sulphonate; sodium tallow alkylsulphonate; and sodium coconut alkyl glyceryl ether sulphonate; and the sodium salt of a sulphated condensation product of tallow alcohol with from about 3 to about 10 moles of ethylene oxide.

It is to be understood that any of the foregoing optional anionic detergent-active compounds can be used separately or as mixtures.

Examples of suitable nonionic detergent-active compounds are condensates of linear and branched-chain aliphatic alcohols or carboxylic acids of from 8 to 18 carbon atoms with ethylene oxide, for instance a coconut alcohol-ethylene oxide condensate of 6 to 30 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensates containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where the group R is an alkyl group of from 10 to 18 carbon atoms and the other is methyl or ethyl, for instance methyltetradecyl sulphoxide.

Suitable cationic detergent-active compounds are quaternary ammonium salts having an aliphatic radical of from 8 to 18 carbon atoms, for instance cetyltrimethylammonium bromide.

Examples of suitable amphoteric detergent-active compounds are derivatives of aliphatic secondary and tertiary amines containing an alkyl group of 8 to 18 carbon atoms and an aliphatic radical substituted by an anionic water-solubilising group, for instance sodium 3-dodecylaminopropionate, sodium 3-dodecylaminopropane sulphonate and sodium N-2-hydroxydodecyl-N-methyltaurate.

Suitable zwitterionic detergent-active compounds are derivatives of aliphatic quaternary ammonium sulphonium and phosphonium compounds having an aliphatic radical of from 8 to 18 carbon atoms and an aliphatic radical substituted by an anionic water-solubilising group, for instance 3-(N,N-dimethyl-N-hexadecylammonium) propane-1-sulphonate betaine, 3-(dodecylmethyl sulphonium) propane-1-sulphonate betaine and 3-(cetylmethylphosphonium) ethane sulphonate betaine.

Further examples of detergent-active compounds are compounds commonly used as surface-active agents given in the well-known textbooks "Surface Active Agents", Volume 1 by Schwartz and Perry and "Surface Active Agents and Detergents", Volume II by Schwartz, Perry and Berch.

The total amount of soap and/or non-soap detergent-active compounds that can be incorporated into deodorant detergent compositions according to the invention is from about 1% to 99% by weight. The preferred amount will depend on the nature of the product (i.e. whether it is liquid or solid and whether it comprises soap or both soap and non-soap detergents).

It can be stated generally that the preferred amount of soap together with optional detergent active compounds to be employed is within the range of from about 5 to about 95% by weight of the composition.

When the deodorant detergent composition is a soap bar it is usually convenient to employ from about 75 to 95% by weight of soap in the bar.

Examples of other deodorant detergent compositions of the invention are non-soap detergent bars, liquid soaps, foam bath and shower products, shampoos, soap, non-soap detergent and nonionic fabric washing powders and liquids, and fabric rinse conditioners.

Deodorant Perfume

The characterisation of the deodorant perfume of the invention presents difficulties, since it cannot be defined solely in terms of substances of specified structure and combinations in specified proportions. Nevertheless, procedures have been discovered that enable the essential materials of the deodorant perfumes to be identified by tests.

The essential materials required for the formulation of deodorant perfumes are those having a lipoxidase-inhibiting capacity of at least 50% or those having a Raoult variance ratio of at least 1.1, as determined by the following tests, which are designated the lipoxidase and morpholine tests respectively.

The Lipoxidase Test

In this test the capacity of a perfume material to inhibit the oxidation of linoleic acid by lipoxidase (E.C. 13.1.13) to form a hydroperoxide is measured.

Aqueous 0.2 M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by weight solution in ethanol of the material to be tested.

A solution of the enzyme lipoxidase in the borate buffer and having an activity within the range of from 15,000 to 40,000 units per ml is prepared.

The activity of the lipoxidase in catalysing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density (OD) at 234 nm within the range of from 0.6 to 1.0 units per minute. The following ingredients are placed in two 3 ml cuvettes:

|  | Control (ml) | Blank (ml) |
|---|---|---|
| Control substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the control cuvette last and the reaction immediately followed spectrophotometrically for about 3 minutes, with recording of the increase in optical density at 234 nm as a curve on a graph.

The capacity of a perfume material to inhibit the oxidation is then measured using a test sample containing enzyme, substrate and a deodorant material. The following ingredients are placed in two 3 ml cuvettes.

|  | Test Sample (ml) | Blank (ml) |
|---|---|---|
| Test substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the perfume material is then calculated from the formula $100(S_1-S_2)/S_1$, where $S_1$ is the slope of the curve obtained with the control and $S_2$ is the slope of the curve obtained with the test sample, and thus expressed as % inhibition. A perfume material that gives at least 50% inhibition in the test is hereafter referred to as having a lipoxidase-inhibiting capacity of at least 50%.

The Morpholine Test

In this test the capacity of a perfume material to depress the partial vapour pressure of morpholine more than that required by Raoult's Law is measured. Substances that undergo chemical reaction with morpholine are to be regarded as excluded from the test, even though they will generally depress the partial vapour pressure of morpholine by at least the defined amount, since not all such substances are operative according to the new principle. It is to be understood, however, that such substances can be included in the formulation of the deodorant perfume, provided that, when included, the composition has the ability to reduce odour intensity by at least 0.50 as herein defined.

The morpholine test is carried out in the following manner:

Into a sample bottle of capacity 20 ml is introduced morpholine (1 g) the bottle fitted with a serum cap and then maintained at 37° C. for 30 minutes for equilibrium to be reached. The gas in the headspace of the bottle is analysed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a pead due to morpholine, the area under which is proportional to the amount of morpholine in the sample.

The procedure is repeated under exactly the same conditions using instead of morpholine alone, morpholine (0.25 g) and the perfume material to be tested (1 g); and also using the perfume material (1 g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol 1, No. 2, 87-91 (1972) and by Jentzsch et al in "Z. Anal. Chem."236, 96-118 (1968).

The measured areas representing the morpholine concentration are proportional to the partial vapour pressure of the morpholine in the bottle headspace. If A is the area under the morpholine peak when only morpholine is tested and A' is the area due to morpholine when a perfume material is present, the relative lowering of partial vapour pressure of morpholine by the perfume material is given by $1-A'/A$.

According to Raoult's Law, if at a given temperature the partial vapour pressure of morpholine in equilibrium with air above liquid morpholine is p, the partial vapour pressure p' exerted by morpholine in a homogeneous liquid mixture of morpholine and perfume material at the same temperature is $pM(M+PC)$, where M and PC are the molar concentrations of morpholine and perfume material. Hence, according to Raoult's Law the relative lowering of morpholine partial vapour pressure $(p-p')/p$, is given by $1-M(M+PC)$, which under the circumstances of the test is $87/(87+m/4)$, where m is the molecular weight of the perfume material.

The extent to which the behaviour of the mixture departs from Raoult's Law is given by the ratio $$\frac{1 - A'/A}{87/(87 + m/4)}$$

The above ratio, which will be referred to as the Raoult variance ratio, is calculated from the test results. Where a material is a mixture of compounds, a calculated or experimentally determined average molecular weight is used for m. A material that depresses the partial vapour pressure of morpholine by at least 10% more than that required by Raoult's Law is one in which the Raoult variance ratio is at least 1.1.

A large number of materials which satisfy one or both tests is described later in this specification and these are hereafter referred to as "components", in contrast to other materials which fail both tests which are referred to as "ingredients".

Before defining the more detailed aspects of deodorant perfumes, it is necessary to clarify some of the terms that will be employed.

A perfume is a blend of organic compounds. For the purposes of this specification it is necessary to identify the "components" in the perfume. This is done by first describing the perfume in terms of four categories. These categories are given below. Examples of "components" in each category are provided.

1. Single chemical compounds whether natural or synthetic, e.g. coumarin (natural or synthetic), isoeugenol, benzyl salicylate. The majority of components are in this category.
2. Synthetic reaction products (products of reaction), mixtures of isomers and possibly homologues, e.g. α-iso-methyl ionone.
3. Natural oils, gums and resins, and their extracts, e.g. patchouli oil, geranium oil, clove leaf oil, benzoin resinoid.
4. Synthetic analogues of category 3. This category includes materials that are not strict analogues of natural oils, gums and resins but are materials that result from attempts to copy or improve upon materials of category 3, e.g. Bergamot AB 430, Geranium AB 76, Pomeransol AB 314.

Components of Categories (3) and (4) although often uncharacterised chemically are available commercially.

Where a material is supplied or used conventionally for convenience as a mixture, e.g. p-t-Amylcyclohexanone diluted with diethyl phthalate, for the present purposes, two components are present, so that use of 5% of a blend of 1 part of this ketone and 9 parts of diethyl phthalate is represented as 0.5% of the ketone and 4.5% of diethyl phthalate.

It has been found necessary when formulating deodorant perfumes for incorporation, for example, into a soap bar, to use components that, as well as satisfying the lipoxidase or morpholine tests, satisfy further rules. These rules are:
(i) there must be at least five components present,
(ii) each of these components must be selected from at least four different chemical classes (to be defined below)
(iii) a component from each of classes 1,2 and 4 must be present,
(iv) at least 45%, preferably at least 50 and most preferably from 60 to 100%, by weight of the deodorant perfume must comprise components. The following provisos also apply:
(a) a component is not considered to contribute to the efficacy of the deodorant perfume if it is present in the deodorant perfume at a concentration of less than 0.5% by weight, and
(b) a class is not considered to contribute to the efficacy of the deodorant perfume it it is present in the deodorant perfume at a concentration of less than 0.5% by weight. The chemical classes, to at least one of which each component must be allocated, are:
Class 1—Phenolic substances;
Class 2—Essential oils, extracts, resins, "synthetic" oils (denoted by "AB");
Class 3—Aldehydes and ketones;
Class 4—Polycyclic compounds;
Class 5—Esters;
Class 6—Alcohols.

In attributing a component to a class, the following rules are to be observed. Where the component could be assigned to more than one class, the component is allocated to the class occurring first in the order given above: for example, clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are components which are present in one or more of the Deodorant Perfume Formulations appearing later in this specification. They either have a lipoxidase-inhibiting capacity (LIC) of at least 50% or have a Raoult variance ratio (RVR) of at least 1.1, or both, and their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavour Chemicals (Aroma Chemicals)" Volume I and II (1969) and the "Perfume & Flavour Materials of Natural Origin (1960) by the same author. Where a component or other ingredient is not described by Arctander, then either the chemical name is given or, where this is not known (such as is the case with perfumery house specialities), then the supplier's identity can be established by reference to the appendix which appears at the end of the specification.

| Class 1 - Phenolic Substances | | | |
|---|---|---|---|
| | LIC | RVR | m |
| iso-Amyl salicylate | 95 | 1.24 | 208 |
| Benzyl salicylate | 0 | 1.58 | 228 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |

| Class 2 - Essential oils, extracts, resins, "synthetic" oils (denoted by "AB") | | | |
|---|---|---|---|
| | LIC | RVR | m |
| Benzoin Siam resinoid | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |

| Class 3 - Aldehydes and Ketones | | | |
|---|---|---|---|
| | LIC | RVR | m |
| 6-Acetyl-1,1,3,4,4,6-hexamethyl-tetrahydronaphthalene | 100 | 1.02 | 258 |
| p-t-Amyl cyclohexanone | 50 | 1.10 | 182 |
| p-t-Butyl-α-methyl hydrocinnamic aldehyde | 74 | — | 204 |
| 2-n-heptylcyclopentanone | 56 | 1.05 | 182 |
| α-iso-Methyl ionone | 100 | 1.13 | 206 |
| β-Methyl naphthyl ketone | 100 | 0.96 | 170 |

| Class 4 - Polycyclic Compounds | | | |
|---|---|---|---|
| | LIC | RVR | m |
| Coumarin | 58 | 1.22 | 146 |
| 1,3,4,6,7,8-Hexahydro-4,6,6,7,8,8-hexamethyl cyclopenta-γ-2-benzopyran | 100 | — | 240 |
| 3a-Methyl-dodecahydro-6,6,9a-trimethyl-naphtho(2,1-b)furan | 58 | 1.30 | 230 |
| β-Naphthyl methyl ether | 100 | — | 158 |

| Class 5 - Esters | | | |
|---|---|---|---|
| | LIC | RVR | m |
| o-t-Butylcyclohexyl acetate | 52 | 1.08 | 198 |
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |
| Phenylethyl phenylacetate | 0 | 1.22 | 241 |

| Class 6 - Alcohols | | | |
|---|---|---|---|
| | LIC | RVR | m |
| Dimyrcetol | 14 | 1.22 | 156 |
| Phenylethyl alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present—the more classes present, the lower the minimum concentration. The minimum average concentration in the various situations that can apply is shown in the Table below:

| Number of classes represented in deodorant perfume | Average concentration of components | |
|---|---|---|
| | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant perfume, but individual components which are present at a concentration of less than 0.5% are eliminated from this calculation, as is the class into which they fall if there is present no component at a concentration of at least 0.5% which falls within that class.

More specifically, the invention also provides a deodorant detergent composition as herein defined wherein the amount of deodorant components in the deodorant perfume present in the classes 1,2 and 4 as herein defined is at least 1%, most preferably at least 3% by weight of the deodorant perfume for each class, and the amount of components present in each of at least two other classes is at least 1% by weight of the perfume, provided also that any component that is present in the deodorant perfume at a concentration of less than a threshold value of 0.5% by weight is eliminated from the calculation of the amounts of components in each class.

Although at least four different classes of components should preferably be represented in the deodorant perfume, superior compositions can be obtained if more than four classes are represented. Accordingly, five or six classes can be represented in the deodorant perfume.

By preparing, examining and testing many hundreds of perfumes, it has been confirmed that it is always necessary to keep within the aforementioned rules when selecting types and amounts of components and ingredients, if a deodorant perfume is to be obtained. Mixtures which do not meet each of the requirements defined by these rules are therefore not deodorant perfumes.

It should be explained that components present in a product such as a soap bar for purposes other than obtaining deodorant effects, for example an adjunct like the antioxidant included in a soap bar for the stabilisation of the soap base, are excluded from the operation of the preceding instructions to the extent that the component is required for that other purpose. The levels at which adjuncts are conventionally present in soap bars is well-established for established materials and readily determinable for new materials so that the application of the above exclusion presents no difficulty.

Deodorant perfumes can be incorporated in deodorant detergent compositions according to the invention, at a concentration of from about 0.01 to about 10%, preferably from 0.5 to 5% and most preferably from 1 to 3% by weight.

It is apparent that if less than 0.01% of a deodorant perfume is employed, then use of the detergent composition containing also a deodorant substance other than a deodorant perfume is unlikely to result in a significant reduction in odour intensity beyond that attributable to the other deodorant substance. If more than 10% of a deodorant perfume is employed, then the deodorant detergent composition might further reduce odour intensity beyond that observed at the 10% level, but use of a composition containing such a high level of perfume could be unpleasant for the user in that it is "overperfumed".

Deodorants other than Deodorant Perfumes

Deodorant substances other than deodorant perfumes which are suitable for use in detergent compositions of the invention are germicides and other substances which are capable of effecting a reduction in odour intensity when tested according to the Odour Reduction Test.

Examples of germicides that can be used are:
2,2'-methylene bis (3,4,6-trichlorophenol)
2,4,4'-trichlorocarbanilide
3,4,4'-trichlorocarbanilide
2,5,4'-tribromosalicylanilide
3-trifluoromethyl-4,4'-dichlorocarbanilide
2,4,4'-trichloro-2'-hydroxydiphenyl ether Other germicides well known for use in detergent products can also be used.

Further examples of other deodorant substances that can be used are zinc salts, such as zinc oxide, and zinc ricinoleate, antioxidants, such as butylated hydroxy anisole and butylated hydroxy toluene, citrate esters such as acetyl tributyl citrate and diols such as 2-ethyl-1,3-hexane diol.

The deodorant detergent composition according to the invention can comprise from 0.1 to 5%, preferably from 0.5 to 3% by weight of deodorant substances other than deodorant perfumes.

Other Detergent Adjuncts

Deodorant detergent compositions of the invention can contain other detergent composition ingredients (adjuncts), for instance sequestrants, builders, superfatting agents, such as free long-chain fatty acids, lather boosters, such as coconut monoethanolamide; lather controllers; inorganic salts such as sodium and magnesium sulphates; moisturisers; plasticisers and thickeners; opacifiers; colourants; bleaches; and fluorescers. Examples of such other detergent adjuncts are given in McCutcheon's "Functional Materials" 1977 Annual published by MC Publishing Co., New Jersey.

The total amount of detergent adjunct that can be incorporated into the deodorant detergent composition according to the invention will normally form the balance of the composition after accounting for the detergent-active compound, the deodorant perfume and other deodorant substance. The detergent adjuncts will accordingly form from 0 to 98.8% by weight of the composition.

Odour Reduction Value

It is a feature of the invention that the deodorant detergent composition has an odour reduction value within the range of from 0.50 and 3.5 as determined by the Odour Reduction Value Test. Preferably, the odour reduction value is at least 0.70, more preferably at least 0.80, and most preferably at least 1.00.

Odour Reduction Value Test

As has been stated, the ability of toilet soap containing both a deodorant perfume and a deodorant other than a deodorant perfume to reduce body malodour was assessed by an odour reduction value test, somewhat similar to that described by Whitehouse and Carter in Proc. Scientific Section of the Toilet Goods Association, 48, 31 (1967) for the measurement of body odour inhibition by germicides in toilet soap.

The test described in that publication was modified in three ways: firstly a 0 to 5 instead of a 0 to 10 grading scale was employed, secondly grading of odour intensity was performed 5 hours after treatment instead of 24 hours, and thirdly, the concentration of deodorant perfume incorporated in the test detergent product was 1.5% by weight of the product.

In this test, the odour reduction value of a standard soap bar containing a deodorant perfume at a standard concentration is measured by assessing its effectiveness in reducing body malodour when the standard soap bar is used to wash the axillae (armpits) of a panel of human subjects.

The choice of a soap base is not critical to the performance of the test but as illustrative of the conduct of the test in this respect the procedure followed in the preparation of the base is included in the description of the test.

Standard soap bars are prepared as follows, all amounts given being by weight.

A soap base there is used a neutral wet sodium soap containing 63% of total fatty matter of which 82% is tallow fatty acid and 18% is coconut oil fatty acid. To a homogeneous mixture of 9000 parts of this soap base and 340 parts of free coconut oil fatty acid at 80° C. are added with mixing, 9.4 parts of a 20% aqueous solution of tetrasodium ethylenediamine tetraacetate, 2.2 parts of a 60% aqueous solution of 1-hydroxyethane-1,1-diphosphonic acid and 7.2 parts of butylated hydroxy toluene (BHT) antioxidant dissolved in a little methylated spirits and the temperature of the mass is raised to 140° C. under superatmospheric pressure. The mass is then sprayed at about 30 mm of mercury, to produce a dried soap composition which is collected and extruded at 30° C. as noodles of about 12% moisture content.

9,770 parts of the soap noodles thus obtained are mixed at ambient temperature with 150 parts of the deodorant perfume to be tested, together with 30 parts of a titanium dioxide opacifier and 50 parts of a colourant suspension. The resulting mixture is milled and stamped into tablets. The deodorant perfume to be tested is therefore present at the standard level of 1.5%.

Control soap bars are prepared in a similar manner except that the deodorant perfume is omitted. In other respects, the control bar should only contain those additives conventionally present in personal washing products and for the purpose in the amount conventionally used in the art.

The test is conducted as follows:

A team of 2 to 4 Caucasian female assessors of age within the range of from 20 to 40 years is selected for olfactory evaluation on the basis that each is able to rank correctly the odour levels of the series of aqueous isovaleric acid solutions listed in Table 2 below, and each is able to detect the reduction in body odour following application to the axillae of human subjects of soap containing 2% germicides, according to the procedure described by Whitehouse and Carter.

A panel of 30 to 50 human subjects for use in the test is assembled from Caucasian male subjects of age within the range of from 20 to 55 years. By screening, subjects are chosen who develop axilliary body malodour that is not usually strong and who do not develop a stronger body malodour in one axilla compared with the other. Subjects who develop unusually strong body malodour, for example due to a diet including curry or garlic, are not selected for the panel.

For two weeks before the start of a test, the panel subjects are assigned a non-deodorant soap bar for exclusive use of bathing and are denied the use of any type of deodorant or antiperspirant. At the end of this period, the subjects are randomly divided into two groups. The control soap bars are then applied to the left axillae of the first group and the right axillae of the second, and the test soap bars are applied to the right axillae of the first group and the left axillae of the second.

The soap bars are applied by a technician using a standard technique in which a wet flannel is soaped with the soap bar for 15 seconds, the axilla is washed with the soaped flannel for 30 seconds, then wiped with a water rinsed flannel and dried with a clean towel. Each subject then puts on a freshly laundered shirt, and 5 hours after application the odour intensity of each subject is assessed, the left axilla of each subject being assessed before the right. The application and assessment are carried out on each of four successive days.

The odour intensity is evaluated by all three assessors who, operating without knowledge of the soap bars used for each subject or the result of evaluation of their fellow-assessors, sniff each axilla and assign a score corresponding to the strength of the odour on a scale from 0 to 5, with 0 corresponding to no odour and 5 representing very strong odour. Before evaluation, each subject stands with his arms against his side: he then raises one arm straight overhead, flattening the axilla vault and making it possible for the assessor's nose to be brought close to the skin, the assessor makes an evaluation and the procedure is repeated with the other axilla.

Standard aqueous solutions of isovaleric acid which correspond to each of the scores 1,2,3,4 and 5 are provided for reference to assist the assessors in the evaluation. These are shown in the table below:

TABLE 2

| Score | Odour Level | Concentrations of aqueous solution of isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each soap bar are averaged and the average score of the test soap bars deducted from the average score of the control soap bars to give the odour reduction value of the deodorant perfume present in the test soap bars.

As a check that the selection of panel subjects is satisfactory for operation of the test, the average score with the control soap bars should be between 2.5 and 3.5.

Although the minimum amount of both the deodorant perfume and the other deodorant substance each comprises at least 0.1% by weight of the deodorant detergent composition, it is their combined effect that enables the detergent composition to reduce body odour intensity by at least 0.50, that distinguishes the invention from the known effect of germicide alone referred to hereinbefore.

Accordingly, if either of the deodorants is employed at a concentration of 0.1%, it may be necessary to ensure that the other is present at a concentration higher than this minimum level in order to provide a detergent composition having an odour reduction value of at least 0.50.

Although the Odour Reduction Value Test referred to herein is used to assess the reduction in odour intensity when the detergent composition is a soap bar, it is to be understood that this method can be adapted to assess the reduction in odour intensity obtainable when other types of detergent composition are used, and that similar odour reduction values will generally be obtained.

Process for Preparing Deodorant Detergent Compositions

The process for preparing deodorant detergent compositions comprises mixing with detergent-active compounds and detergent adjuncts, from 0.1 to 10% by weight of a deodorant perfume, and from 0.1 to 5% by weight of another deodorant to provide a deodorant detergent composition which has an odour reduction value of at least 0.50 as measured by the odour reduction value test. The selection of detergent active compounds and detergent adjuncts and their respective amounts employed in the process of the invention will depend upon the nature of the required detergent composition (e.g. solid or liquid) and the purpose for which it is required (e.g. for personal washing or shampooing).

The invention in particular provides a process for making soap tablets which comprise mixing with detergent active compounds, detergent adjuncts, a deodorant perfume and a germicide or a mixture of germicides and/or another deodorant such as zinc oxide.

Usually it is convenient to add the deodorant perfume and other deodorant substance to the detergent composition at a stage towards the end of its manufacture so that loss of any volatile ingredients such as may occur during a heating step is minimised.

It is furthermore usual to incorporate the deodorant perfume and other deodorant substances in such a manner that they are thoroughly mixed with the other ingredients and are uniformly distributed throughout the detergent composition. It is however also possible, particularly with solid products such as marbled soap bars and speckled or spotted solid or liquid products, to provide detergent compositions where the deodorant perfume and/or the deodorant other than deodorant perfume is not uniformly and homogeneously mixed with the other ingredients of the detergent composition, and is concentrated in the marbled bands or the speckled or spotted parts of such products.

EXAMPLES OF THE INVENTION

The invention is illustrated by the following Examples, in which all parts and percentages are by weight.

EXAMPLE 1

In this example the combined effect of a deodorant perfume and zinc oxide as another deodorant substance together incorporated in a soap bar was evaluated by the Odour Reduction Value Test described above.

Soap bars for use as control bars and also as a basis for incorporation of the deodorant perfume and zinc oxide had the following constituents:

|  | % |
|---|---|
| Sodium soap (containing 4 parts tallow fatty acid to 1 part coconut fatty acid) | 87.84 |
| Ethylene diamine tetracetic acid | 0.03 |
| 1-hydroxyethane-1,1-diphosphonic acid | 0.02 |
| Butylated hydroxy toluene | 0.11 |
| Water | 12 |

Test soap bars were prepared by the addition of 1.5 parts of a deodorant perfume and 0.9 parts zinc oxide to 97.6 parts of the above soap base.

The formulation of the deodorant perfume was as follows:

| Deodorant Perfume Formulation 1 | | | |
|---|---|---|---|
| | Parts | Class | Total in class |
| Components | | | |
| iso-Amyl salicylate | 5.0 | 1 | |
| Benzyl salicylate | 4.0 | 1 | 10.25 |
| LRG 201 | 1.25 | 1 | |
| Bergamot AB 430 | 15.0 | 2 | |
| Geranium AB 76 | 4.0 | 2 | 20.7 |
| Opoponax resinoid | 1.7 | 2 | |
| 1,3,4,6,7,8-Hexahydro-4,6,6,7,8,8-hexamethylcyclopenta-γ-2-benzopyran | 10.0 | 4 | 10.0 |
| o-t-Butylcyclohexyl acetate | 0.5 | 5 | |
| | | | 4.25 |
| Diethyl phthalate | 3.75 | 5 | |
| Nonanolide-1,4 | 0.2* | (5) | |
| Ingredients | | | |
| Amber AB 358 | 3.0 | | |
| Benzyl alcohol | 0.15 | | |
| Cedar atlas oil | 5.0 | | |
| Citronellol | 7.0 | | |
| Citronella oil | 16.1 | | |
| Citronellyloxyacetaldehyde | 0.5 | | |
| Hexyl aldone | 0.7 | | |
| Jasmin AB 284 | 12.0 | | |
| Orange oil sweet | 8.0 | | |
| 10-Undecen-1-al | 0.15 | | |
| Vetyvert oil | 2.0 | | |
| | 100.0 | | |

*eliminated from calculation - below threshold value of 0.5% (proviso (a)).

Perfume Formulation 1 is a deodorant perfume, since each of the rules is satisfied as follows:

| (i) Total number of components present | 9 |
|---|---|
| (ii) Number of different classes represented | 4 |
| (iii) Classes represented Nos. 1,2,4&5 | |
| (iv) Total amount of components present | 45.2 |

| Odour Reduction Value Test Results | | |
|---|---|---|
| Product | Mean Score | Difference (Control-Test) |
| Control soap | 2.78 | |
| Test soap | 1.85 | 0.93 |

The Odour Reduction Value of the test soap bar containing Deodorant Perfume 1 and zinc oxide was 0.93.

This was well in excess of 0.50 which defines the lower limit of reduction of odour intensity (odour reduction value) of compositions of the invention.

EXAMPLE 2

In this example the combined effect of a deodorant perfume and the germicide, 3.4.4'-trichlorocarbanilide, as another deodorant substance together incorporated in a soap bar prepared as described in Example 1 was evaluated by the Odour Reduction Test.

Test soap bars were prepared by the addition of 1.5 parts of a deodorant perfume and 0.75 parts of 3,4,4'-trichlorocarbanilide to 97.75 parts of the soap base.

The formulation of the deodorant perfume was as follows:

| Deodorant Perfume Formulation 2 | | | |
|---|---|---|---|
| | Parts | Class | Total in class |
| Components | | | |
| Carvacrol | 3.5 | 1 | |
| | | | 4.5 |
| Thyme oil red | 1.0 | 1 | |
| Bergamot AB 37 | 20.0 | 2 | |
| Pomeransol AB 314 | 6.0 | 2 | 30.0 |
| Petitgrain oil | 4.0 | 2 | |
| 6-Acetyl-1,1,3,4,4,6-hexamethyl-tetrahydronaphthalene | 3.0 | 3 | |
| | | | 8.0 |
| β-Methyl naphthyl ketone | 5.0 | 3 | |
| 3a-Methyl-dodecahydro-6,6,9a-trimethyl naphtho-2(2,1-b)furan | 0.25* | (4) | |
| β-Naphthyl methyl ether | 9.0 | 4 | 9.0 |
| Ingredients | | | |
| Citronellyl acetate | 5.0 | | |
| Dipropylene glycol | 4.75 | | |
| Geranyl nitrile | 1.5 | | |
| Indole | 1.0 | | |
| Lemongrass oil | 3.0 | | |

Deodorant Perfume Formulation 2

|  | Parts | Class | Total in class |
|---|---|---|---|
| Lime AB 402 | 10.0 | | |
| Lavandin oil | 4.0 | | |
| l-Menthol | 8.0 | | |
| Neroli AB 78 | 6.0 | | |
| Orange oil sweet | 5.0 | | |
| | 100.0 | | |

*eliminated from calculation - below threshold value of 0.5%.

Perfume Formulation 2 is a deodorant perfume, since each of the rules is satisfied as follows:

| (i) Number of components present | 8 |
|---|---|
| (ii) Number of different classes represented | 4 |
| (iii) Classes represented, Nos. 1,2,3&4 | |
| (iv) Total amount of components present | 51.5 |

Odour Reduction Value Test Results

| Product | Mean Score | Difference (Control-Test) |
|---|---|---|
| Control soap | 2.97 | |
| Test soap | 2.45 | 0.52 |

The Odour Reduction Value of the test soap bar containing Deodorant Perfume 2 and the germicide was 0.52. This was above 0.50 which defines the lower limit of reduction of odour intensity (odour reduction value) of compositions of the invention.

EXAMPLE 3

In this example the combined effect of a deodorant perfume and the germicide, 2,4,4'-trichloro-2'-hydroxydiphenyl ether, as another deodorant substance together incorporated in a soap bar prepared as described in Example 1 was evaluated by the Odour Reduction Test.

Test soap bars were prepared by the addition of 1.5 parts of a deodorant perfume and 0.25 parts of 2,4,4'-trichloro-2'-hydroxydiphenyl ether to 98.25 parts of the soap base.

The formulation of the deodorant perfume was as follows:

Deodorant Perfume Formulation 3

| | Parts | Class | Total in class |
|---|---|---|---|
| Components | | | |
| Mousse de chene Yugo | 1.25 | 1 | |
| Pimento leaf oil | 10.0 | 1 | 11.25 |
| Benzoin Siam resinoid | 5.0 | 2 | |
| Bergamot AB 430 | 15.0 | 2 | 25.0 |
| Geranium oil | 5.0 | 2 | |
| p-t-Amylcyclohexanone | 5.0 | 3 | |
| | | | 17.0 |
| α-iso-Methyl ionone | 12.0 | 3 | |
| Coumarin | 4.0 | 4 | |
| 1,3,4,6,7,8-Hexahydro-4,6,6,7,8,8-hexamethylcyclopenta-γ-2-benzopyran | 3.0 | 4 | 7.0 |
| Diethyl phthalate | 4.35 | 5 | 4.35 |
| Ingredients | | | |
| Hercolyn D | 12.25 | | |
| Lavandin oil | 10.0 | | |

Deodorant Perfume Formulation 3 (continued)

| | Parts | Class | Total in class |
|---|---|---|---|
| Musk ambrette | 3.0 | | |
| Rosenta AB 380 | 10.0 | | |
| Rose-D-oxide | 0.15 | | |
| | 100.0 | | |

Perfume Formulation 3 is a deodorant perfume, since each of the rules is satisfied as follows:

| (i) Number of components present | 10 |
|---|---|
| (ii) Number of different classes represented | 5 |
| (iii) Classes represented, Nos. 1,2,3,4&5 | |
| (iv) Total amount of components present | 64.6 |

Odour Reduction Value Test Results

| Product | Mean Score | Difference (Control-Test) |
|---|---|---|
| Control soap | 3.28 | |
| Test soap | 2.78 | 0.50 |

The Odour Reduction Value of the test soap bar containing Deodorant Perfume 3 and the germicide was 0.50. This defines the lower limit of reduction of odour intensity (odour reduction value) of compositions of the invention.

EXAMPLE 4

In this example the combined effect of a deodorant perfume and the germicide, 2,4,4'-trichloro-2'-hydroxydiphenyl ether and 3,4,4'-trichlorocarbanilide, as other deodorant substances together incorporated in a soap bar prepared as described in Example 1 was evaluated by the Odour Reduction Value test.

Test soap bars were prepared by addition of 1.5 parts of a deodorant perfume, 0.5 parts of 2,4,4'-trichloro-2'-hydroxydiphenyl ether and 1.5 parts of 3,4,4'-trichlorocarbanilide to 92.5 parts of the soap base together with 4 parts of polyethylene glycol 1000.

The formulation of the deodorant perfume was as follows:

Deodorant Perfume Formulation 4

| | Parts | Class | Total in class |
|---|---|---|---|
| Components | | | |
| Ethyl vanillin | 0.2* | (1) | |
| iso-Eugenol | 5.0 | 1 | 6.25 |
| LRG 201 | 1.25 | 1 | |
| Bergamot AB 430 | 8.0 | 2 | |
| | | | 15.0 |
| Patchouli oil | 7.0 | 2 | |
| 2-n-Heptylcyclopentanone | 0.5 | 3 | |
| | | | 5.5 |
| α-iso-Methyl ionone | 5.0 | 3 | |
| β-Naphthyl methylether | 7.5 | 4 | 7.5 |
| p-t-Butylcyclohexyl acetate | 4.3 | 5 | |
| Diethyl phthalate | 8.25 | 5 | |
| i-Nonyl formate | 5.0 | 5 | 26.55 |
| Nonanediol-1,3-diacetate | 4.0 | 5 | |
| Phenylethyl phenyl acetate | 5.0 | 5 | |
| Tetrahydro muguol | 6.0 | 6 | 6.0 |
| Ingredients | | | |
| Citronella oil | 6.0 | | |
| Green Herbal AB 502 | 15.0 | | |

-continued

Deodorant Perfume Formulation 4

| | Parts | Class | Total in class |
|---|---|---|---|
| Indole | 1.5 | | |
| Rosenta AB 380 | 6.0 | | |
| Sandalone | 4.0 | | |
| γ-Undecalactone | 0.5 | | |
| | 100.0 | | |

*eliminated from calculation - below threshold value of 0.5%.

Perfume Formulation 4 is a deodorant perfume, since each of the rules is satisfied as follows:

| (i) Number of components present | 14 |
|---|---|
| (ii) Number of different classes represented | 6 |
| (iii) Classes represented, Nos: 1,2,3,4,5&6 | |
| (iv) Total amount of components present | 66.8 |

Odour Reduction Value Test Results

| Product | Mean Score | Difference (Control-Test) |
|---|---|---|
| Control soap | 3.22 | |
| Test soap | 2.10 | 1.12 |

The Odour Reduction Value of the test soap bar containing Deodorant Perfume 4 and the germicides was 1.12. This was well in excess of 0.50 which defines the lower limit of reduction of odour intensity (odour reduction value) of compositions of the invention.

EXAMPLE 5a

In this example the combined effect of a deodorant perfume and acetyltributyl citrate as another deodorant substance together incorporated in a soap bar prepared as described in Example 1 was evaluated by the Odour Reduction Value Test.

Test soap bars were prepared by the addition of 1.5 parts of a deodorant perfume and 0.75 parts of acetyltributyl citrate to 97.75 parts of the soap base.

The formulation of the deodorant perfume was as follows.

Deodorant Perfume Formulation 5

| | Parts | Class | Total in class |
|---|---|---|---|
| Components | | | |
| Benzyl salicylate | 15.0 | 1 | 21.0 |
| Mousse de chene Yugo | 6.0 | 1 | |
| Bergamot AB 430 | 15.0 | 2 | 15.0 |
| 6-Acetyl-1,3,3,4,4,6-hexamethyl-tetrahydronaphthalene | 2.5 | 3 | 2.5 |
| p-t-Amylcyclohexanone | 0.06 | (3) | |
| 3a-Methyl-dodecahydro-6,6,9a-trimethyl-naptho-2(2,1-b)furan) | 0.75 | 4 | 0.75 |
| Diethyl phthalate | 8.04 | 5 | 8.04 |
| Nonanolide-1,4 | 0.2* | (5) | |
| Dimyrcetol | 16.0 | 6 | 16.0 |
| Ingredients | | | |
| Cinnamic alcohol | 5.0 | | |
| Dimethyl benzyl carbinyl acetate | 2.5 | | |
| Dipropylene glycol | 14.25 | | |
| Geraniol | 5.0 | | |
| iso-Butyl phenyl acetate | 5.0 | | |
| Methyl salicylate | 0.5 | | |
| Pelargene | 4.0 | | |
| Trichloromethyl phenyl carbinyl | | | |

-continued

Deodorant Perfume Formulation 5

| | Parts | Class | Total in class |
|---|---|---|---|
| acetate | 0.2 | | |
| | 100.0 | | |

*eliminated from calculation - below threshold value of 0.5%.

Perfume Formulation 5 is a deodorant perfume, since each of the rules is satisfied as follows:

| (i) Number of components present | 7 |
|---|---|
| (ii) Number of different classes represented | 6 |
| (iii) Classes represented, Nos: 1,2,3,4,5&6 | |
| (iv) Total amount of components present | 63.29 |

Odour Reduction Value Test Results

| Product | Mean Score | Difference (Control-Test) |
|---|---|---|
| Control soap | 3.26 | |
| Test soap | 2.54 | 0.72 |

The Odour Reduction Value of the test soap bar containing Deodorant Perfume 5 and the citrate was 0.72. This was well in excess of 0.50 which defines the lower limit of reduction of odour intensity (odour reduction value) of compositions of the invention.

EXAMPLE 5b

In this example the combined effect of a deodorant perfume and ethyl hexane diol as another deodorant substance together incorporated in a soap bar prepared as described in Example 1 was evaluated by the Odour Reduction Test.

Test soap bars were prepared by the addition of 1.5 parts of a deodorant perfume and 1 part of 2-ethyl-1,3-hexane diol to 97.5 parts of the soap base.

The formulation of the deodorant perfume was the same as that used in Example 5a.

Odour Reduction Value Test Results

| Product | Mean Score | Difference (Control-Test) |
|---|---|---|
| Control soap | 3.02 | |
| Test soap | 2.39 | 0.63 |

The Odour Reduction Value of the test soap bar containing Deodorant Perfume 5 and the diol was 0.63. This was well in excess of 0.50 which defines the lower limit of reduction of odour intensity (odour reduction value) of compositions of the invention.

EXAMPLE 6

In this example the combined effect of a deodorant perfume and butylated hydroxytoluene as another deodorant substance together incorporated in a soap bar prepared as described in Example 1 was evaluated by the Odour Reduction Value Test.

The test soap bars were prepared by addition of 1.5 parts of a deodorant perfume and 1 part of butylated hydroxytoluene to 97.5 parts of the soap base.

The formulation of the deodorant perfume was as follows:

| Deodorant Perfume Formulation 6 | | | |
|---|---|---|---|
| Components | Parts | Class | Total in class |
| Clove leaf oil | 10.0 | 1 | 11.25 |
| LRG 201 | 1.25 | 1 | |
| Petitgrain oil | 10.0 | 2 | 10.0 |
| p-t-Butyl-α-methyl hydro cinnamic aldehyde | 15.0 | 3 | 15.0 |
| 3a-Methyl-dodecahydro-6,6,9a-tri-methylnaphtho-2(2,1-b)furan | 0.5 | 4 | 0.5 |
| o-t-Butylcyclohexyl acetate | 2.0 | 5 | |
| Diethyl phthalate | 9.25 | 5 | 21.25 |
| i-Nonyl acetate | 10.0 | 5 | |
| Phenyl ethyl alcohol | 10.0 | 6 | 10.0 |
| Ingredients | | | |
| Benzyl Propionate | 4.0 | | |
| Bergamot oil | 15.0 | | |
| Dimethyl benzyl carbinyl acetate | 5.0 | | |
| iso-Butyl benzoate | 5.0 | | |
| Neroli oil | 3.0 | | |
| | 100.0 | | |

Perfume Formulation 6 is a deodorant perfume, since each of the rules is satisfied as follows:

| | | |
|---|---|---|
| (i) Number of components present | 9 | |
| (ii) Number of differrent classes represented | 6 | |
| (iii) Classes represented, Nos: 1,2,3,4,5&6 | | |
| (iv) Total amount of components present | 68.0 | |

| Odor Reduction Value Test Results | | |
|---|---|---|
| Product | Mean Scores | Difference (Control-Test) |
| Control soap | 2.97 | |
| Test soap | 2.17 | 0.80 |

The Odour Reduction Value of the test soap bar containing Deodorant Perfume 6 and the other deodorant was 0.80. This was well in excess of 0.50 which defines the lower limit of reduction of odour intensity (odour reduction value) of compositions of the invention.

APPENDIX

The following glossary provides a further information, including the suppliers' names, which will aid identification of some of the aforementioned perfume components and ingredients.

All materials which are classified by a name and number are obtainable from Proprietary Perfumes Limited.

| | |
|---|---|
| Dimyrcetol | Dimyrcetol (IFF) |
| Hercolyn D | Tetrahydro abietate + dihydro abietate (HP) |
| LRG 201 | Oakmoss speciality (RB) |
| Pelargene | Pelargene (PPL) |
| Rose-D-Oxide | Rose oxide synthetic (PPL) |
| Sandalone | Sandalone (PPL) |

Perfume Houses

HP—Hercules Powder Co.
IFF—International Flavour & Fragrances Inc.
RB—Roure Bertrand
PPL—Proprietary Perfumes Limited

What is claimed is:

1. A deodorant soap composition comprising:
   (i) from about 1 to about 99% by weight of soap;
   (ii) from 0.01 to about 10% by weight of a deodorant perfume;
   (iii) from 0.1 to about 5% by weight of a deodorant other than a deodorant perfume selected from the group consisting of germicides, zinc salts, zinc oxide, antioxidants, citrate esters, diols and mixtures thereof; and
   (iv) from 0 to 98.8% by weight of detergent adjunct other than included in (iii); the deodorant perfume comprising from 45 to 100% by weight of deodorant components, said components having a lipoxidase-inhibiting capacity of at least 50% or a Raoult variance ratio of at least 1.1, said components being classified into six classes consisting of:

Class 1: phenolic substances,
   Class 2: essential oils, extracts, resins and synthetic oils,
   Class 3: aldehydes and ketones,
   Class 4: polycyclic compounds,
   Class 5: esters
   Class 6: alcohols, provided that where a component can be classified into more than one class, it is placed in the lower or lowest numbered class;
   said components being so selected that
   (a) the deodorant perfume contains at least five components of which at least one must be selected from each of Class 1, Class 2 and Class 4;
   (b) the deodorant perfume contains components from at least 4 of the 6 classes; and
   (c) any component present in the deodorant perfume at a concentration of less than 0.5% by weight of said composition is eliminated from the requirements of (a) and (b);

the composition having an Odour Reduction Value within the range of from 0.50 to 3.5 as measured by the Odour Reduction Value Test.

2. A composition according to claim 1, which has an Odour Reduction Value of at least 0.70.

3. A composition according to claim 1, which has an Odour Reduction Value of at least 1.00.

4. The composition according to claim 1, wherein the amount of deodorant components present in said class comprising phenolic substances and said class comprising essential oils, extracts, resins and synthetic oils and said class comprising polycyclic compounds, is at least 1% by weight of the deodorant perfume for each of said classes, and the amount of deodorant components present in said further class chosen from the remaining three classes is at least 1% by weight of the deodorant perfume.

5. The composition according to claim 1, wherein the average concentration of all such components present is at least 5% by weight where four of said classes is represented, or at least 4.5% by weight where five or six of said classes are represented.

6. The composition according to claim 1, wherein the amount of deodorant components present in said class comprising phenolic substances and said class comprising essential oils, extracts, resins and synthetic oils and said class comprising polycyclic compounds, is at least 3% by weight of the deodorant perfume for each of said classes and the amount of deodorant components present in said further class chosen from the remaining three classes is at least 3% by weight of the deodorant perfume.

7. The composition according to claim 1, wherein at least five of the classes is represented.

8. The composition according to claim 1, wherein all six classes are represented.

9. A composition according to claim 1 wherein the deodorant other than a deodorant perfume is the germicide 3,4,4'-trichlorocarbanilide.

10. A composition according to claim 1, wherein the deodorant other than a deodorant perfume is the germicide 2,4,4'-trichloro-2'-hydroxydiphenyl ether.

11. A composition according to claim 1, wherein the deodorant other than a deodorant perfume is the antioxidant butylated hydroxytoluene.

12. A composition according to claim 1, wherein the deodorant other than a deodorant perfume is the citrate ester acetyl tributyl citrate.

13. A composition according to claim 1, wherein the deodorant other than a deodorant perfume is the diol 2-ethyl-1,3-hexane diol.

14. The composition according to claim 1 which additionally comprises a non-soap detergent active compound, the total amount of soap and non-soap detergent active compound forming from 1 to 99% by weight of the composition.

15. The composition according to claim 1, wherein the soap forms from about 5 to about 95% by weight of the composition.

16. The composition according to claim 1, wherein the soap forms from about 75 to about 95% by weight of the composition.

17. A deodorant toilet soap bar comprising:
(i) from about 75 to about 95% by weight of soap;
(ii) from about 0.01 to about 10% by weight of a deodorant perfume;
(iii) from 0.1 to 5% by weight of a deodorant other than a deodorant perfume selected from the group consisting of:
2,2'-methylene bis (3,4,6-trichlorophenol),
2,4,4'-trichlorocarbanilide,
3,4,4'-trichlorocarbanilide,
2,5,4'-tribromosalicylanilide,
3-trifluoromethyl-4-4'-dichlorocarbanilide,
2,4,4'-trichloro-2'-hydroxydiphenyl ether,
zinc oxide,
zinc ricinoleate,
butylated hydroxy anisole,
butylated hydroxy toluene,
acetyl tributyl citrate,
2-ethyl-1,3-hexane diol,
and mixtures thereof;
(iv) from 0 to 98.8% by weight of detergent adjunct other than included in (iii); the deodorant perfume comprising from 45 to 100% by weight of deodorant components, said components having a lipoxidase-inhibiting capacity of at least 50% or a Raoult variance ratio of at least 1.1, said components being classified into six classes consisting of:
Class 1: phenolic substances,
Class 2: essential oils, extracts, resins and synthetic oils,
Class 3: aldehydes and ketones,
Class 4: polycyclic compounds,
Class 5: esters,
Class 6: alcohols, provided that where a compound can be classified into more than one class, it is placed in the lower or lowest numbered class;
said components being so selected that
(a) the deodorant perfume contains at least five components of which at least one must be selected from each of Class 1, Class 2 and Class 4;
(b) the deodorant perfume contains components from at least 4 of the 6 classes; and
(c) any component present in the deodorant perfume at a concentration of less than 0.5% by weight of said composition is eliminated from the requirements of (a) and (b);
the composition having an Odour Reduction Value within the range of from 0.50 to 3.5 as measured by the Odour Reduction Value Test.

18. A method for suppressing human body malodor which comprises applying to the skin or hair an effective amount of the deodorant detergent composition according to claim 1.

19. A process for preparing a deodorant detergent composition according to claim 1, said process comprises mixing a deodorant perfume and a deodorant other than a deodorant perfume and a detergent active compound to provide a deodorant detergent composition having an Odour Reduction Value within the range of from 0.50 to 3.5 as measured by the Odour Reduction Value Test.

* * * * *